United States Patent
Mamayek et al.

(10) Patent No.: US 8,123,774 B2
(45) Date of Patent: Feb. 28, 2012

(54) PIEZOELECTRIC VASCULAR IMPLANT RELEASE DEVICE

(75) Inventors: Don Mamayek, Mountain View, CA (US); Stephen Christopher Porter, Oakland, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2429 days.

(21) Appl. No.: 10/393,791

(22) Filed: Mar. 20, 2003

(65) Prior Publication Data

US 2004/0186464 A1    Sep. 23, 2004

(51) Int. Cl.
*A61M 29/00* (2006.01)
*A61B 17/32* (2006.01)

(52) U.S. Cl. ........ 606/194; 606/108; 606/169; 623/1.11

(58) Field of Classification Search .................. 623/1.11, 623/1.12; 606/108, 169, 191–200, 127, 128
See application file for complete search history.

(56) References Cited

U.S. PATENT DOCUMENTS

| | | |
|---|---|---|
| 4,427,609 A | 1/1984 | Broussoux et al. |
| 4,560,737 A | 12/1985 | Yamamoto et al. |
| 4,592,880 A | 6/1986 | Murakami |
| 4,668,449 A | 5/1987 | Soni et al. |
| 4,743,252 A | 5/1988 | Martin, Jr. et al. |
| 5,122,136 A | 6/1992 | Guglielmi et al. |
| 5,234,437 A | 8/1993 | Sepetka |
| 5,250,071 A | 10/1993 | Palermo |
| 5,262,926 A | 11/1993 | Hall |
| 5,269,291 A * | 12/1993 | Carter ........................... 606/128 |
| 5,304,195 A | 4/1994 | Twyford, Jr. et al. |
| 5,311,884 A | 5/1994 | Scopelianos |
| 5,312,415 A | 5/1994 | Palermo |
| 5,350,397 A | 9/1994 | Palermo et al. |
| 5,354,295 A | 10/1994 | Guglielmi et al. |
| 5,522,879 A | 6/1996 | Scopelianos |
| 5,645,564 A | 7/1997 | Northrup et al. |
| 5,722,979 A * | 3/1998 | Kusleika ...................... 623/1.11 |
| 5,856,722 A | 1/1999 | Haronian et al. |
| 5,873,835 A | 2/1999 | Hastings et al. |
| 5,944,750 A | 8/1999 | Tanner et al. |
| 5,957,940 A | 9/1999 | Tanner et al. |
| 6,022,369 A * | 2/2000 | Jacobsen et al. ............... 606/191 |
| 6,024,718 A | 2/2000 | Chen et al. |
| 6,063,101 A * | 5/2000 | Jacobsen et al. ............. 623/1.11 |
| 6,344,041 B1 * | 2/2002 | Kupiecki et al. ............... 606/191 |
| 6,346,091 B1 | 2/2002 | Jacobsen et al. |
| 6,371,919 B1 | 4/2002 | Tanner et al. |
| 6,447,542 B1 | 9/2002 | Weadock |
| 6,486,588 B2 | 11/2002 | Doron et al. |
| 6,504,286 B1 | 1/2003 | Porat et al. |
| 6,607,553 B1 * | 8/2003 | Healy et al. ................... 623/1.11 |
| 2002/0099408 A1 * | 7/2002 | Marks et al. ................... 606/200 |
| 2002/0188311 A1 | 12/2002 | Ferrera et al. |

OTHER PUBLICATIONS

PCT International Search Report for PCT/US03/38461, Applicant: Scimed Life Systems, Inc., Forms PCT/ISA/210 and 220, dated Jul. 27, 2004 (7 pages).

* cited by examiner

*Primary Examiner* — David Shay
(74) *Attorney, Agent, or Firm* — Vista IP Law Group LLP

(57) ABSTRACT

The present invention relates to a devices and methods for their use for the release of medical workpieces such as, without limitation, embolic devices, from apparatuses used to deliver them to a target site in a patient's body involving use of a piezoelectric member that is fracturable and/or an adhesive layer that is susceptible to adhesive or cohesive failure.

23 Claims, 5 Drawing Sheets

PIEZOELECTRIC VASCULAR IMPLANT RELEASE DEVICE

FIELD OF THE INVENTION

The present invention relates to the fields of medicine, medical devices and material science. More particularly, it relates to a piezoelectric device useful for releasing medical workpieces, in particular embolic devices, at a target site in a patient's body.

BACKGROUND OF THE INVENTION

Numerous types of implantable medical workpieces are in common use today. Some of these, such as stents and shunts, are implanted surgically, that is, the operating physician surgically accesses the target site and implants the device by hand. Others, such as embolic and brachytherapy devices are more often attached to the end of a delivery apparatus, which is then directed to the target site, whereupon the device is detached and deposited at the site. An example of such a delivery apparatus is a steerable catheter. The medical workpiece is placed at the distal end of a pusher wire that can be threaded through a lumen in the catheter. The catheter is steered to the target site, the pusher wire, with the workpiece attached, is threaded through the catheter lumen and out into the target site. There, the connection between the implant and the pusher wire is severed, the wire and catheter are withdrawn and the workpiece is implanted.

A great deal of effort has gone into devising ways of effecting the separation of a medical workpiece from the delivery apparatus. Mechanical (U.S. Pat. No. 5,234,437 (unscrews), U.S. Pat. No. 5,250,071 (clasp unhooks), U.S. Pat. No. 5,261,916 (key removed from slot), U.S. Pat. No. 5,304,195 (ball disengages from sleeve), U.S. Pat. No. 5,312,415 (device pushed off guidewire) and U.S. Pat. No. 5,350,397 (ball dislodged from socket)), electrolytic (U.S. Pat. Nos. 5,122,136 and 5,354,295), and vibrational energy (U.S. Pat. Nos. 6,022,369 and 6,346,091 B1 (vibration ruptures connection) means have been disclosed. While each of these is relatively effective, each has its shortcomings. Mechanical means often involve substantial movement of the separating elements possibly resulting in misplacement of the implant. Electrolytic means limit the materials that can be used in the construction of the delivery apparatus, may generate undesirable particulates, are often difficult to control, require a grounding needle inserted in the flesh of the patient and require careful insulation of components to avoid electrolysis at sites other than the desired point of separation. Vibrational force generated at the proximal end of the delivery apparatus must travel to the other end with attendant dissipation of the energy that may affect reliability and also may produce particulate matter when separation occurs.

What is needed is a device/method for separating a medical workpiece from a delivery apparatus that is rapid, reliable, efficient and involves minimum manipulation at the point of separation. The present invention provides such a device and method.

SUMMARY OF THE INVENTION

Thus, in one aspect, the present invention relates to a device for releasing a medical workpiece at a target site in a patient's body, comprising: a delivery apparatus comprising an elongate member having a proximal and a distal end; a piezoelectric member having a proximal and a distal end, the proximal end being directly or operatively coupled to the elongate member at or near its distal end; at least two electrical conducting members, each having a distal end electrically coupled to the piezoelectric member and a proximal end electrically coupled to a signal generator; and, a medical workpiece having a proximal and a distal end, the proximal end being directly or operatively coupled to the distal end of the piezoelectric member.

In an aspect of this invention, the elongate member is a pusher wire.

In an aspect of this invention, the elongate member is a microcatheter.

In an aspect of this invention, the electrical conducting members comprise electrically conductive wires.

In an aspect of this invention, the pusher wire comprises one of the electrical conducting members.

In an aspect of this invention, the piezoelectric member is operatively coupled to the medical workpiece through an adhesive layer disposed between the piezoelectric member and the workpiece, the adhesive layer comprising a proximal face that forms a first interfacial bond with a distal face of the piezoelectric member and a distal face that forms a second interfacial bond with a proximal face of the workpiece.

In an aspect of this invention, the adhesive layer is susceptible to adhesive and/or cohesive failure.

In an aspect of this invention, adhesive failure comprises failure of the interfacial bond between the piezoelectric member and the adhesive layer, failure of the interfacial bond between the adhesive layer and the workpiece, or both.

In an aspect of this invention, cohesive failure comprises fracturing of the adhesive layer.

In an aspect of this invention, the adhesive layer comprises one or more engineered structural flaws.

In an aspect of this invention, the engineered structural flaw(s) comprise(s): one or more discontinuities in one or more faces of the adhesive layer; one or more internal discontinuities in the adhesive layer; or, a combination of one or more face discontinuities and one or more internal discontinuities in the adhesive layer.

In an aspect of this invention, the adhesive layer is selected from the group consisting of a glass, a ceramic, a metal and a polymer.

In an aspect of this invention, the piezoelectric substance is fracturable.

In an aspect of this invention, the fracturable piezoelectric substance comprises one or more engineered structural flaws.

In an aspect of this invention, the engineered structural flaw(s) comprise(s): one or more discontinuities in one or more faces of the piezoelectric substance; one or more internal discontinuities in the structure of the piezoelectric member, wherein the discontinuities begin at one face of the piezoelectric member and terminate within the member, begin at one face and terminate at another face of the member, begin and terminate entirely within the internal structure of the member, or a combination of these; or, a combination or one or more discontinuities in one or more faces and one or more discontinuities in the internal structure of the piezoelectric member.

In an aspect of this invention, the piezoelectric member comprises a piezoelectric substance selected from the group consisting of a piezoelectric crystal, a piezoelectric ceramic and a piezoelectric polymer.

In an aspect of this invention, either the distal end of the piezoelectric member or the distal end of the elongate member comprises a first coupling structure; and, the proximal end of the medical workpiece comprises a second coupling structure that is at least partially complementary to the first coupling structure, wherein, when the second coupling structure is in complementary alignment with the first coupling structure, the medical workpiece is releasably coupled, directly or operatively, to the delivery apparatus.

In an aspect of this invention, either the first or the second coupling structure comprises a protrusion surface that has a selected shape; and, the other coupling structure comprises a cavity surface that is at least partially complementary to the protrusion surface.

In an aspect of this invention, the protrusion surface comprises a cylinder, a cone or a truncated cone; and, the cavity surface defines a cylindrical, conical or truncated-conical void.

In an aspect of this invention, the protrusion surface comprises a sphere having a diameter and the cavity comprises at least one cross-sectional dimension of which is complementary to the diameter of the sphere.

In an aspect of this invention, the device further comprises a lumen described by an inside surface of the piezoelectric member, the lumen being disposed in the piezoelectric member such that an axis thereof aligns with the medical workpiece; and, a plunger member having a proximal and a distal end, the plunger being slidably disposed within the lumen, wherein at least one cross-sectional dimension of the plunger is complementary to at least one cross-sectional dimension of the lumen such that when no electrical signal is being sent to the piezoelectric member, the plunger is releasably coupled, directly or operatively, to the piezoelectric member.

In an aspect of this invention, the device further comprises a cavity surface defining a cavity in the distal portion of the elongate member; and, an actuator member that is either slidably disposed within the cavity or is coupled to the cavity surface, the actuator also being directly or operatively coupled to the piezoelectric member, wherein at least a portion of the distal end of the elongate member comprises the first coupling structure.

In an aspect of this invention, the device further comprises a cavity surface defining a cavity in the distal portion of the piezoelectric member, wherein at least a portion of the distal end of the piezoelectric member comprises the first coupling structure.

An aspect of this invention comprises a method for delivering a medical workpiece to a target site in a patient, comprising: providing a delivery apparatus comprising an elongate member having a proximal and a distal end; providing a piezoelectric member having a proximal and a distal end, the proximal end of the piezoelectric member being directly or operatively coupled to the elongate member at or near its distal end; providing at least two electrical conducting members, each having a distal end electrically coupled to the piezoelectric member and a proximal end electrically coupled to a signal generator; providing a medical workpiece having a proximal and a distal end, the proximal end being directly or operatively coupled to the distal end of the piezoelectric member; directing the distal end of elongate member to the target site; positioning the workpiece at or in the target site; generating an electrical signal; and, transmitting the electrical signal through the electrical conducting members to the piezoelectric member, thereby effecting release of the medical workpiece.

In an aspect of this invention, providing a delivery apparatus comprises providing a microcatheter.

In an aspect of this invention, providing a delivery apparatus comprises providing a pusher wire.

In an aspect of this invention, the electrical conducting members comprise electrically conducting wires.

In an aspect of this invention, operatively coupling the piezoelectric member to the medical workpiece comprises providing an adhesive layer disposed between piezoelectric member and the workpiece, the adhesive layer comprising a proximal face that forms a first interfacial bond with a distal face of the piezoelectric member and a distal face that forms a second interfacial bond with a proximal face of the workpiece.

In an aspect of this invention, the method further comprises providing the adhesive layer with an engineered structural flaw that renders it susceptible to fracture.

In an aspect of this invention, providing the adhesive layer with an engineered structural flaw comprises: creating one or more discontinuities in one or more faces of the adhesive layer; creating one or more internal discontinuities in the adhesive layer; or, creating a combination of one or more facial discontinuities and one or more internal discontinuities in the adhesive layer.

In an aspect of this invention, the method further comprises providing the piezoelectric member with one more engineered structural flaws.

In an aspect of this invention, providing the piezoelectric member with one or more engineered flaws comprise(s): creating one or more discontinuities in one or more faces of the piezoelectric member; creating one or more internal discontinuities in the structure of the piezoelectric, wherein the discontinuities begin at one face of the member and terminate within the member, begin at one face, pass through the member and terminate at another face, begin and terminate entirely in the internal structure of the member, or a combination of these; or, a combination of one or more discontinuities in one or more faces, and one or more discontinuities in the internal structure, of the piezoelectric member.

In an aspect of this invention, the method further comprises providing the distal end of the piezoelectric member with a first coupling structure and providing the proximal end of the workpiece with a second coupling structure that is at least partially complementary to the first coupling structure such that, when no electrical signal is being generated, the piezoelectric member is releasably coupled, directly or operatively, to the workpiece.

In an aspect of this invention, the method further comprises providing the piezoelectric member with an inside surface that defines a lumen, an axis of which aligns with the medical workpiece and providing a plunger member that is slidably disposed in the lumen, wherein at least one cross-sectional dimension of the plunger is complementary to at least one cross-sectional dimension of the lumen such that, when no electrical signal is being sent to the piezoelectric member, the plunger is releasably coupled, directly or operatively, to the piezoelectric member.

In an aspect of this invention, the method further comprises providing the piezoelectric member with a cavity surface that defines a cavity, wherein at least a portion of the cavity surface is complementary to at least a portion of a surface of the medical workpiece such that, when the two portions are in complementary alignment, the medical workpiece is releasably coupled to the piezoelectric member; and, essentially completely filling the cavity with a non-compressible liquid.

In an aspect of this invention, the method further comprises providing the distal portion the elongate member with a cavity surface that defines a cavity and that is at least partially complementary to a surface of the medical workpiece such that, when the cavity surface and the medical workpiece surface are in complementary alignment, the medical workpiece is releasably coupled to the elongate member; providing an actuator member that is either slidably disposed in or coupled to the cavity surface and that is also directly or operatively coupled to the piezoelectric member; and, essentially filling the cavity with a non-compressible fluid.

An aspect of this invention, the target site is an aneurysm, an arteriovenous malformation, a fistula or a tumor and the medical workpiece is an embolic device.

DETAILED DESCRIPTION OF THE INVENTION

Brief Description of the Drawings

The drawings herein are provided solely for the purpose of assisting the reader in understanding the present invention. They are not intended, nor should they be construed, as limiting the scope of this invention in any manner whatsoever. For example, in the drawings and discussion thereof, the electrodes are shown and described as being embedded in the piezoelectric member. It is entirely possible, and is within the scope of this invention, to simply attach the electrodes to a surface of the piezoelectric member. Also, the male/female complementary structures are shown with the male structure being part of the piezoelectric member and the female a part of the medical workpiece. This relationship can be reversed such that the male structure is on the medical workpiece and the female structure is a part of the piezoelectric member. Other such variations will become apparent to those skilled in the art based on the disclosures herein; all such variations are within the scope of this invention.

DEFINITIONS

Figure 1:
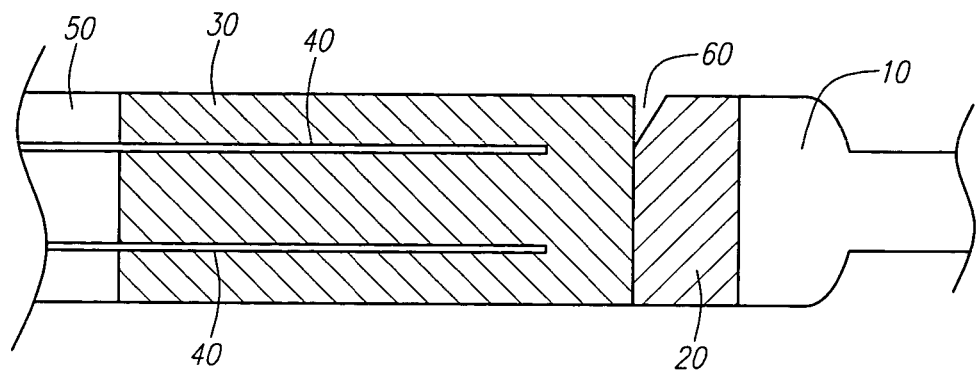
FIG. 1 is a schematic representation of an embodiment of this invention. It shows a piezoelectric member bonded to a medical workpiece by an adhesive layer in which a flaw has been purposely engineered into its surface. When an electrical signal is sent to the electrodes embedded in the piezoelectric member, the flaw serves as a site of initiation of a catastrophic failure of the adhesive layer.

As used herein, the phrase "medical workpiece" refers to any manner of medical device that is meant to be implanted at a site in a patient's body wherein to get the device to the target site requires a delivery apparatus to which the device is attached and, when in place, detached. Medical workpieces include, without limitation, embolic devices, stents and brachytherapy devices.

As used herein, a "piezoelectric member" refers to a piezoelectric crystal, piezoelectric ceramic, piezoelectric polymer or composites thereof.

As used herein, "adhesive failure" refers to the breakdown of the interfacial bond between an adhesive layer and a structure to which it is bonded. For example, when two structures are "glued" together, the glue comprises an adhesive layer, one surface of which forms a bond with a surface of one of the structures and a second surface of which forms a bond with a surface of the other structures. The breaking of either or both of these bonds constitutes adhesive failure.

As used herein, "cohesive failure" refers to breakdown of the intermolecular forces that hold the elements of a substance together. The substance in the present invention is the adhesive layer or the material of which the piezoelectric member is constructed. As used herein, cohesive failure may entail a complete disintegration of a substance to molecular level such as would be the case if the adhesive layer or some portion thereof were to dissolve in a solvent, partial disintegration of a substance to a particulate level or the fracturing of the substance, the latter being presently preferred.

As used herein, the term "fracturing" or "fractured" or "fracturable" refers to the cohesive failure of a structure whereby the structure breaks into at least two pieces, one of which is attached, directly or indirectly, to the delivery apparatus and one of which is attached to the medical workpiece. It is presently preferred that the structure in fact breaks into two pieces only. If more than one piece is produced, it is presently preferred that the pieces be of such a small size that they are readily purged from the system by normal physiological processes, e.g., flowing blood, etc. Fracturing may result from the natural brittleness of a substance from which a structure is constructed, such as, without limitation, glasses and some polymers or it may result from the inclusion of engineered structural flaws at which fracturing will be initiated when a stress is applied to the structure.

As used herein "catastrophic failure" refers to a failure, either cohesive or adhesive, that results in a structure breaking apart into at least two pieces, one of which includes the delivery apparatus and one of which includes the medical workpiece.

As used herein, an "engineered structural flaw" refers to a discontinuity in a structure that, when the structure is stressed, initiates catastrophic failure of the structure. Examples of engineered structural flaws include, without limitation, grooves, notches or scoring in an exterior surface of a structure, voids or holes in an otherwise solid internal structure, holes that originate at an outer surface of a structure and penetrate into the interior but do not go completely through the structure, holes that originate at one surface then penetrate through the structure and end at another surface, etc.

As used herein, a "discontinuity" in a surface or internal structure refers to a disruption in the overall structure or the surface or internal structure. Externally, the disruption generally involves, without limitation, one or more scratches, grooves, notches, holes, channels, etched patterns and the like or a combination of these and an internal disruption generally involves some kind of void, be it a hole extending from a surface, an entirely internal void or a combination of these.

As used herein, the term "complementary" refers to two structures that, when placed a particular alignment, have one or more surfaces that come in, or in very close proximity to, physical contact such that the two structures can be coupled, either by frictional forces if the surfaces actually contact, or by the inclusion of an inter-surface bond such as, without limitation, a spot weld or a small region comprising an adhesive layer. One of the structures can be referred to as the "protrusion surface," which refers to a solid shape that can be inserted into the other structure, a void called herein a "cavity surface" in which case, if the surfaces are "complementary," they can be aligned such that at least a portion of the protrusion surface is in contact with or close proximity to at least a portion of the cavity surface. When two surfaces are in such contact or close proximity, they are said to be "in complementary alignment."

As used herein, "substantially completely," when referring to the degree of filling of the chamber in an embodiment hereof means at least 95% filled, preferably at least 98% filled and most preferably at least 99.5% filled.

As used herein, the phrase, "directly or operatively coupled" refers to a situation wherein one member of a device herein is related to another member in one of two ways. First, one member can be in direct physical contact with the other member in which case the members are "directly coupled." Alternatively, the another structure that might be another member or the device such as, without limitation, an actuator disposed between a piezoelectric member and a fluid that itself is in contact with a medical workpiece, or it might be a non-member component of the device such as, without limitation, a spot weld or partial adhesive layer, that is so disposed. When the members are "operatively coupled," essentially the same effect is transmitted from one component to the other component as would be the case when the members are in direct contact; that is, the intervening component acts as a conduit for the desired operational effect.

As used herein, the phrase, "electrically coupled" refers to the situation wherein one component of a device herein is in direct or operational contact with another component such that an electrical signal applied to the component is transmitted to the member to which it is electrically coupled.

When it is stated herein that an axis of a lumen aligns with a medical workpiece, it means that a line drawn down the centerline of the lumen intersects some point on the surface of the medical workpiece.

A "non-compressible" fluid refers to a fluid that does not suffer a change in volume upon the application of an external pressure useful in the application of the invention herein; i.e., up to 100 atmospheres. For the purposes of this invention, most liquids, including, without limitation, water constitute non-compressible fluids.

As used herein, an "embolic device" refers to a device that, when implanted in a patient's body, acts as a nucleus for the formation of a thrombus that eventually occludes the region around the device. An example, without limitation of an embolic device is a platinum coil that, when inserted in an aneurysm in a patient's blood vessel causes eventual occlusion of the aneurysm such that bleeding from the aneurysm is prevented or at least ameliorated should it rupture.

DISCUSSION

Piezoelectricity or, synonymously, the piezoelectric effect was discovered by Pierre and Jacques Curie in 1880. The effect is manifested by the appearance of an electric potential across the faces of some materials when they are placed under pressure. When, on the other hand, a piezoelectric material (PEM) is subjected to an electric field, physical stresses are created in the material that distorts it, a phenomenon known as the converse piezoelectric effect. It is the converse piezoelectric effect that the device of this invention makes use.

Hundreds of PEMs are currently known. Among these are crystalline substances whose unit crystal structure lacks a center of symmetry. Examples, without limitation of such substances are tourmaline, Rochelle salt and quartz. Polycrystalline substances which have been placed in a polarized state can also exhibit a piezoelectric effect and are called piezoelectric ceramics. Examples of piezoelectric ceramics include, without limitation, barium titanate ($BaTiO_3$) and lead zirconium titanate (PZT, $PbZrTiO_3$). In addition to piezoelectric crystals and ceramics, a number of polymeric materials are known to exhibit a piezoelectric effect. Most notable among these is polyvinylidene fluoride (PVDF) which was discovered by Kawai in 1969 and is still today the polymer that exhibits the strongest piezoelectric effect. Some co-polymers of PVDF, such as poly(PVDF-co-trifluoroethylene) and poly(PVDF-co-tetrafluoroethylene) are also piezoelectric. Other polymers that exhibit a piezoelectric effect include, without limitation, polyparaxylene, poly(bischloromethyloxetane) (Penton), aromatic polyamides, polysulfone, polyvinyl fluoride, synthetic polypeptides and cyanoethylcellulose.

PEMs have many diverse uses. For example and without limitation, PEMs are used in thin film capacitors, non-volatile ferroelectric semi-conductor memory, optical wave guides, optical memory and display, SAW (surface acoustic wave) devices, medical ultrasound applications, gas igniters, displacement transducers, accelerometers, transformers, impact printer heads and inkjet printer heads. The present invention makes use of the converse piezoelectric effect to release implantable medical workpieces such as, without limitation, embolic and brachytherapy devices at specific target locations in a patient's body.

Figure 8A:
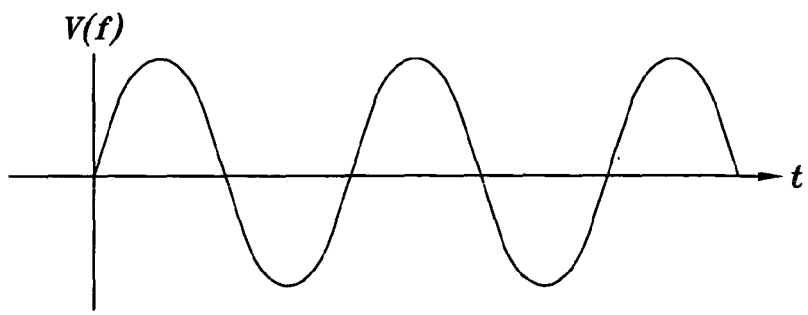
FIG. 8 is a schematic representation of some exemplary wave forms of electrical signals that can be used to generate a converse piezoelectric effect in a piezoelectric member of a device of this invention.
Figure 8B:
Figure 8C:
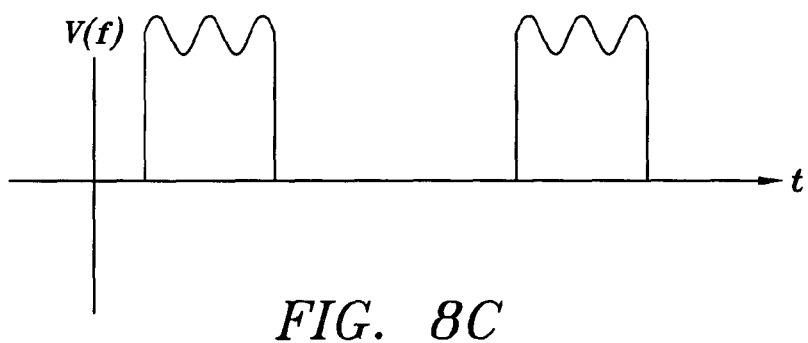
Figure 8D:
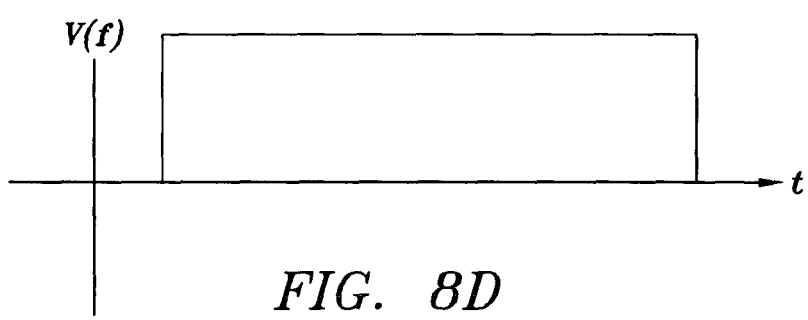

The electrical signal sent to the piezoelectric member may constitute any number of waveforms. For example, without limitation, the signal may consist of a single DC pulse (FIG. 8D), multiple DC pulses (FIG. 8B), a continuous sinusoidal signal (FIG. 8A) or an oscillating square wave signal (FIG. 8C). Any type of signal may be employed that will initiate the converse piezoelectric effect in the piezoelectric member. Many signal types other than those exemplified herein will become apparent to those skilled in the art based on the disclosures herein and all such signal types are within the scope of this invention.

FIG. 1 is a schematic of a release device of this invention. Medical workpiece 10 is bonded to piezoelectric member 30 by adhesive layer 20. Electrodes 40 are embedded in piezoelectric member 30. Electrodes 40 are attached to an electric signal generator by electrical conductors such as, without limitation, electrically conducting wires. The electrodes may be separate entities from the electrical conductors or, as, for example without limitation, in the case of wires, may simply be the bare ends of the wires, as shown in FIG. 1. Furthermore, if the particular embodiment of this invention includes a pusher wire, that wire can also serve as one of the electrical conductors. Adhesive layer 20 has an engineered flaw 60 in its exterior surface. While the engineered flaw is shown as a notch in one surface of adhesive layer 20, any of the above mentioned engineered structural flaws may be used. Furthermore, the "notch" may extend completely around the outer surface of adhesive layer 20 and comprise a groove in the surface. In addition, internal engineered structural flaws such as those discussed below with respect to flaws engineered into the piezoelectric member may also be incorporated into adhesive layer 20. The key is that, when an electric signal is sent to electrodes 40 such that piezoelectric member 30 undergoes a converse piezoelectric effect, the engineered structural flaw or flaws (since one or more such flaws may be engineered into the layer), initiate catastrophic failure of the adhesive layer such that workpiece 10 is completely separated from delivery apparatus 50. Catastrophic failure occurs most readily in substances such as glasses, which are naturally brittle, and polymers that have a glass transition temperature that is higher than the temperature of working environment of the device, that is, above body temperature, which will differ depending on the patient but for humans is approximately 98.6° F. Some representative polymers that may be used include, without limitation, poly(methyl methacrylate), poly(ethylene terphthalate), polystyrene and poly(styrene-co-acrylonitrile).

In addition, the adhesive layer may comprise a material that is soluble in water but which dissolves at a very slow rate in a static environment, that is, when a structure made of the material is stationary in water or blood. However, when the structure is made to oscillate, such as would be the case if a pulsed electrical signal were supplied to the piezoelectric member, a surface of which the adhesive layer is bonded to, the rate of dissolution of the material at the surface would be increased many-fold such that catastrophic failure of the adhesive layer would occur very rapidly, preferably in a matter of seconds. Examples of materials that would be expected to have the requisite characteristic are, without limitation, poly(ethylene oxide), poly(propylene oxide), poly(vinylpyrrolidone), poly(vinyl alcohol) and copolymers and blends thereof.

Piezoelectric member 30 is attached to delivery apparatus 50. Delivery apparatus 50 may be any apparatus known to those skilled in the art. Examples, without limitation, of such apparatuses are a catheter with a lumen through which a pusher wire, with the device of this invention attached to its distal end, can be threaded, a microcatheter wherein the piezoelectric member is attached, directly or indirectly, to the distal end of the catheter etc. It is emphasized that the invention herein will work with any delivery apparatus that can be used to direct an implantable medical workpiece to a target site in a patient's body and all such delivery apparatuses are within the scope of this invention.

Figure 2:
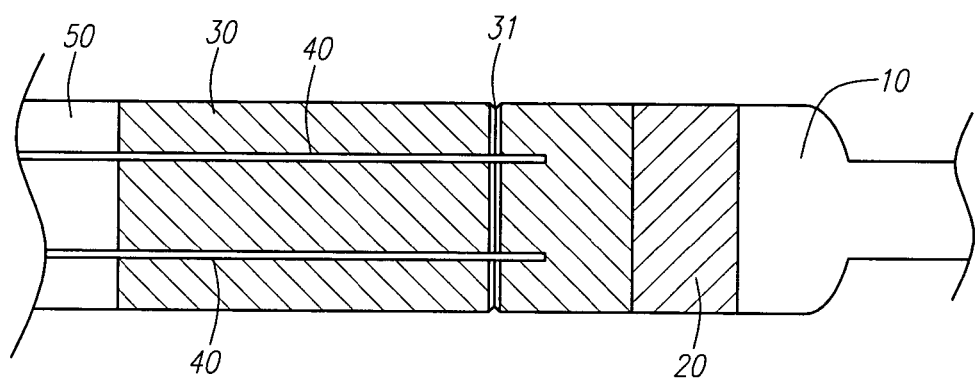
FIG. 2 is a schematic representation of another embodiment of this invention. It shows a piezoelectric member that itself contains an engineered flaw in its surface. An electrical signal is sent to the electrodes in (or on) the piezoelectric member initiating catastrophic failure of the piezoelectric member which fragments into, preferably, two pieces, one of which comprises the medical workpiece detached from the delivery apparatus.

FIG. 2 is a schematic representation of another aspect of this invention. Once again, medical workpiece 10 is bonded to piezoelectric member 30 by adhesive layer 20 and the opposite end of piezoelectric member 30 is attached to delivery apparatus 50. Electrodes 40 are embedded in piezoelectric member 30. In this aspect, however, rather than including engineered structural flaws in the adhesive layer, flaw 31 (or flaws, since more than one can be incorporated into piezoelectric member 30), are engineered into the piezoelectric member itself. Thus, when an electrical signal is sent to electrodes 40, piezoelectric member 30 undergoes a converse piezoelectric effect and, as the result of the engineered structural flaw 31, is subjected to catastrophic failure. As described above, this means that the member fractures into at least two pieces, such that medical workpiece 10 is completely separated from delivery apparatus 50. Of course, piezoelectric member 30 may fracture into more than two pieces; regardless of how many pieces member 30 breaks into, the result must be that workpiece 10 is completely severed from delivery apparatus 50. It is presently preferred, however, that piezoelectric member 30 fracture into two pieces. As shown in FIG. 2, engineered structural flaw 31 is a groove etched in and circumnavigating the outer surface of member 30. While engineered flaw 31 is shown as being essentially perpendicular to the longitudinal axis of member 30, this is not necessarily the case. It could be parallel to the longitudinal axis or at an angle other than 90° thereto. Likewise, it may or may not extend around the entire circumference of member 30. Those skilled in the art will, based on the disclosures herein and without undue additional experimentation, be able to design countless types of engineered structural flaws in the surface of member 30 that will result in its catastrophic failure upon application of an electrical signal to electrodes 40 and the initiation thereby of a converse piezoelectric effect in member 30. All such designs are within the scope of this invention.

Figure 3:
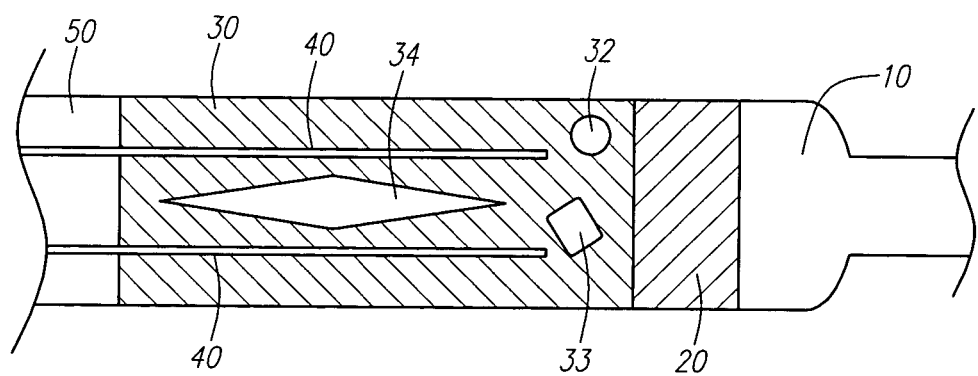
FIG. 3 is a schematic representation of yet another embodiment of this invention. It shows a piezoelectric member into the interior of which various structural flaws have been engineered. The shape and placement of the flaws are such that catastrophic failure of the piezoelectric member will occur when an electrical signal is sent to the electrodes embedded in the member. The placement, size, shape and positioning of the flaws in the figure are for illustrative purposes only and are not intended, and should not be construed, as describing or suggesting a particular size, shape or location of a flaw. Proper flaw design and placement will be determined by the nature of the piezoelectric member itself, i.e., the material of which it is manufactured, it's dimensions, the level of signal to be provided, etc. The determination of these criteria will be well within the ability of those skilled in the art based on the disclosures herein and all such flaws are within the scope of this invention.

For example, FIG. 3 shows other types of engineered structural flaws that should be useful with the device of this invention. Again, medical workpiece 10 is bonded to piezoelectric member 30 through adhesive layer 20. Piezoelectric member 30 is also attached to delivery apparatus 50. Electrodes 40 are embedded in piezoelectric member 30. Here, rather than having engineered structural flaws in an outer surface of member 30, the flaws are internal and include a lozenge-shaped void 34, a void of circular cross-section 32 and a parallelepiped-shaped void 33. The number, shape and location of each engineered structural flaws that will result in catastrophic failure of member 30 when an electrical signal is sent to electrodes 40 will be readily empirically determinable by those skilled in the art based on the disclosures herein; those shown in FIG. 3 are not intended, nor should they be construed, as limiting this invention in any manner whatsoever. For instance, without limitation, one or more of the internal flaws shown in FIG. 3 could be combined with one or more surface flaws such that shown in FIG. 2. In addition, flaws that initiate at a surface and penetrate into the internal structure of member 30 as well as those that penetrate completely through the structure may be used. In general, it is known that flaws with sharp edges and changes of direction are most conducive to catastrophic failure of a piezoelectric substance upon application of an electrical signal and initiation of the converse piezoelectric effect; such flaws are presently preferred.

Figure 4:
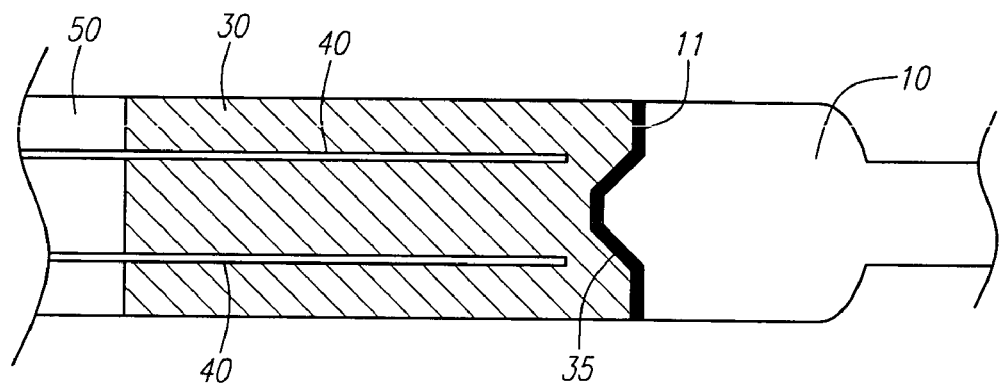
FIG. 4 is a schematic representation of still another embodiment of this invention. It shows a piezoelectric member that has a particular shape, in this case a truncated conical cavity, at one end. The medical workpiece has a complementary shape, a truncated cone, at one end. When brought into alignment, the complementary shapes are bound together. Such binding, without limitation, can be the result of frictional forces generated by contact of complementary surfaces or can be the result of "spot welding," i.e., one or more small areas of physico-chemical bonding of complementary surfaces of the piezoelectric member and the medical workpiece. An electrical signal is sent to the electrodes in the piezoelectric member causing it to deform and pull away from the medical workpiece, breaking the frictional grip, the physico-chemical bond, etc. and allowing the workpiece to separate from the delivery apparatus.

FIG. 4 is a schematic representation of yet another aspect of this invention. In this aspect, piezoelectric member 30 has structural feature 35 at one of its surfaces. Here structural feature 35 is shown as a truncated conical depression in a surface of member 30. Medical workpiece 10 has a complementary feature 11 at one of its surfaces. When features 11 and 35 are brought into complementary juxtaposition, they bind together due either to frictional forces between the surfaces of the features or, if desired, by the inclusion of small areas of inter-surface bonding as by, for instance without limitation, spots of solder or other adhesive material between the complementary surfaces. It is to be noted that complementarity refers to the structure of the features only when piezoelectric member 30 is not undergoing a converse piezoelectric effect for, when an electrical signal is sent to electrodes 40 and member 30 does undergo a converse piezoelectric effect, the distortion of member 30 caused by the converse effect destroys the complementarity of the features allowing workpiece 10 to separate from member 30. While complementary features 11 and 35 are shown to be a truncated conical depression and projection in FIG. 4, it is understood that almost unlimited variations on this theme are possible. The only constraint is that the complementary shapes permit workpiece 10 to remain coupled to piezoelectric member 30 under static conditions but to separate when a converse piezoelectric effect is created in piezoelectric member 30. This, of course, means that the location of the shapes may be reversed as well. That is, rather than the cavity appearing in the piezoelectric element and the protrusion on the medical workpiece, the protrusion could be a feature of the piezoelectric element and the cavity a feature of the medical workpiece. These and other variations on the above embodiments will become apparent to those skilled in the art based on the disclosures herein; all such variations are within the scope of this invention.

Figure 5:
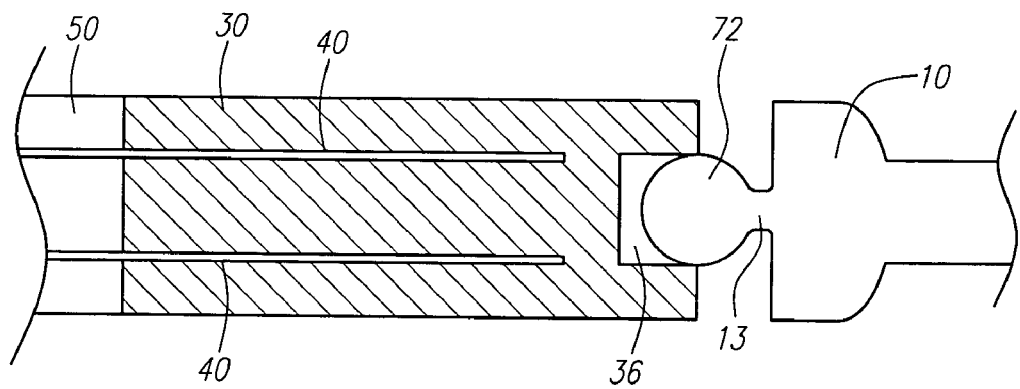
FIG. 5 is a schematic representation of a further embodiment of this invention. It shows a variation on the theme of the device depicted in FIG. 4. Whereas in FIG. 4 the shape of the piezoelectric member and that of the medical workpiece were essentially completely complementary, i.e., all surfaces of the shapes were complementary, in the device of FIG. 5, the piezoelectric member is shown with a rectangular cross-section cavity and the medical workpiece with a spherical projection. The diameter of the ball complements the length of at least one edge of the rectangle such that, when the ball is inserted in the cavity, it becomes bound there as the result of frictional forces, a spot weld, a bit of adhesive, etc. An electrical signal sent to the electrodes of the piezoelectric member causes it to deform thus releasing the ball and the medical workpiece.

For example, FIG. 5 is a schematic depiction of a quite different approach to complementary features that also should be useful in the present invention. Here, rather than essentially complete complementarity wherein all surfaces of the depression in piezoelectric member 30 are complemented by a surface of the projection on medical workpiece 10, only certain aspects of the surfaces are complementary. That is, the depression in piezoelectric member 30 is a rectangular parallelepiped 36. The projection on workpiece 10, on the other hand is spherical. Complementarity is found in the diameter of sphere 12 and the length of at least one of the sides of parallelepiped 36. When sphere 12 is inserted into parallelepiped 36, a region of its circumference comes in contact, or near contact, with a surface of depression 36 and the sphere is held there, as above, by frictional forces, an inter-surface bond such as, without limitation, a solder point, a spot of adhesive, etc. When an electrical signal is sent to electrodes 40, piezoelectric member 30 undergoes an converse piezoelectric effect, is distorted thereby and releases sphere 12 and medical workpiece 10. As mentioned above, the spherical structure could just as well be a feature of piezoelectric member 30 and the rectangular parallelepiped a feature of medical workpiece 10.

Figure 6A:
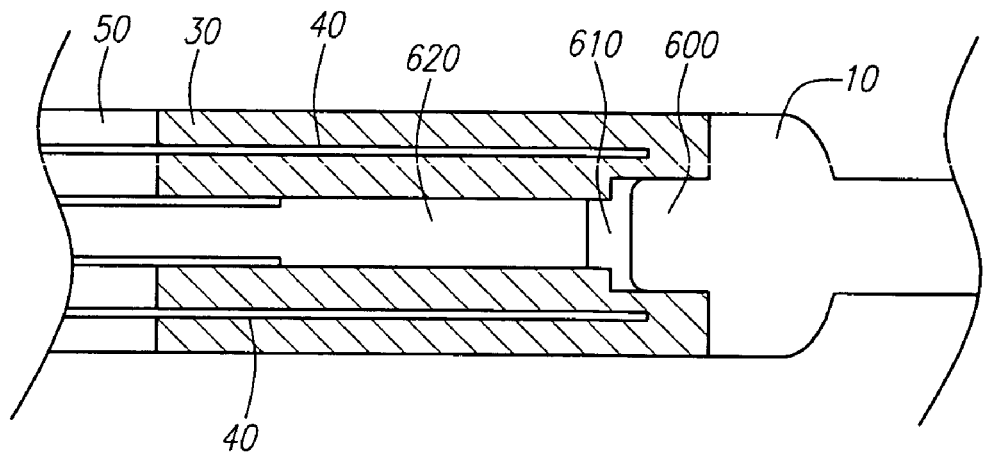
FIG. 6 is a schematic representation of a further embodiment of this invention and shows a means for separating a medical workpiece from a piezoelectric member involving a plunger member which is held in check within the piezoelectric member until a converse piezoelectric effect is generated in the member at which time the plunger is released, impacts a protrusion on the medical workpiece and pushes it away from the apparatus.
Figure 6B:
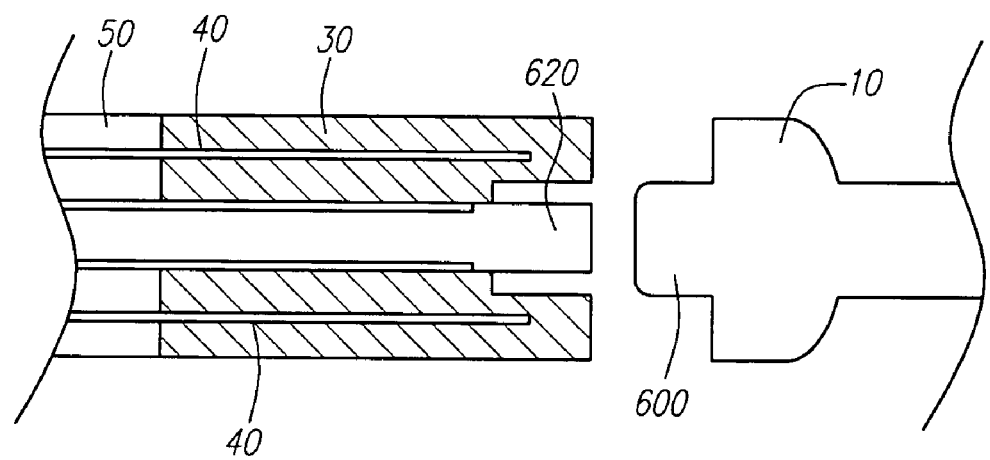

FIG. 6 shows another approach to effecting the separation of a piezoelectric member from a medical workpiece. In FIG. 6A, medical workpiece 10 has a protruding feature 600 that is complementary to cavity 610 in piezoelectric member 30. Piezoelectric member 30 contains a plunger member 620, which is operationally coupled to the proximal end of delivery apparatus 50. When activated by the operator, plunger member 620 moves distally and pushes medical workpiece 10 away from the apparatus (FIG. 6B). The distance that plunger member 620 can travel can, if desired, be set such that, at its furthest distal projection, it does not protrude beyond the end of piezoelectric member 30 as shown.

Figure 7A:
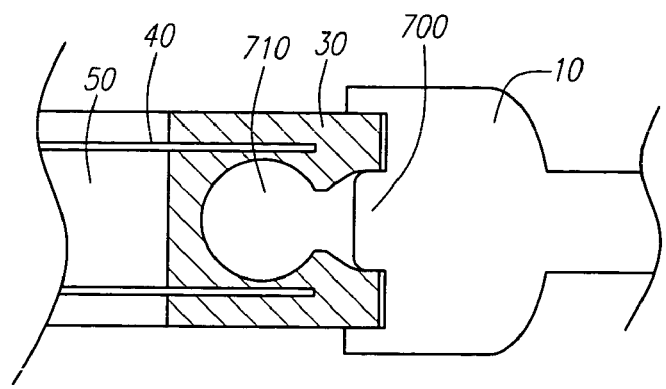
In FIG. 7A, the piezoelectric member is shown with a cavity that is filled with a non-compressible fluid. Application of a converse piezoelectric effect causes the piezoelectric member to contract and thereby cause the non-compressible fluid to exert pressure on the protrusion on the medical workpiece resulting in its expulsion/release from the delivery apparatus (FIG. 7B).
Figure 7B:
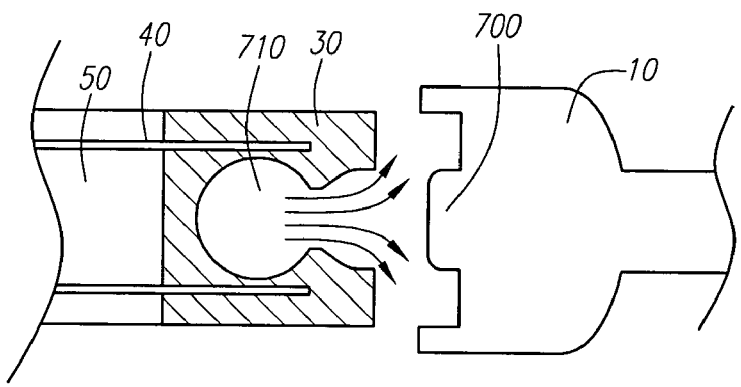
FIG. 7 is a schematic representation of yet another embodiment of this invention.
FIG. 7C is a schematic representation of another embodiment of this invention wherein the piezoelectric member does not itself incorporate the chamber in which the liquid resides but rather, much like a piezoelectric printhead, exerts a pressure on an actuator, which then deforms and applies pressure to the liquid, which, in turn applied pressure to the medical workpiece, resulting in its ejection.

FIG. 7 shows a still further means by which a piezoelectric member might be separated from a medical workpiece. In FIG. 7A, medical workpiece 10 is shown with protruding features 700 and 720, which, as noted above, may be of any shape that results in medical workpiece 10 being coupled to piezoelectric member 30 in the absence of an electrical signal. Piezoelectric member 30 is shown with an at least partially complementary feature that holds medical workpiece 10 in place and with a cavity 710 which is filled with a non-compressible fluid. Protruding feature 710 or 720 or may, but need not necessarily, be in sufficiently tight contact with the complementary feature of piezoelectric member 30 that a fluid-tight compartment comprising cavity 710 is created. That is, it is possible to employ a fluid of sufficient viscosity that, even if the fit between protruding feature 710 or 720 and the complementary feature of piezoelectric member 30 are not literally fluid-tight, no or minimal fluid escapes the system prior to the application of an electrical signal to the piezoelectric member and when such signal is applied, pressure is exerted on the fluid too rapidly for it to dissipate by leakage of fluid around the complementary features. Thus, when an electrical signal is provided to piezoelectric member 30, the volume of cavity 710 is reduced which causes the non-compressible fluid to exert pressure on medical workpiece 10, pushing it out and away from piezoelectric member 30.

Figure 7C:
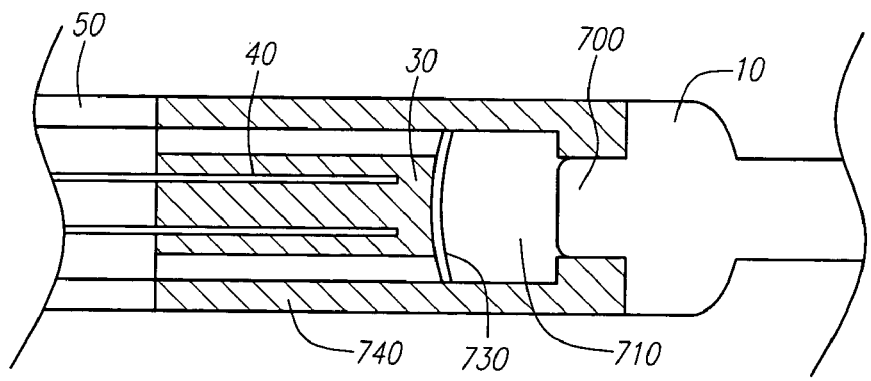

FIG. 7C shows another means by which a medical workpiece my be separated from a delivery apparatus through use of a piezoelectric member. In FIG. 7C, piezoelectric member 30 is in contact with actuator 730 that, along with medical workpiece 10 protrusion 700 forms cavity 710. As above, the cavity may, but need not, be fluid-tight. In this instance, when an electric signal is provided to piezoelectric member 30, it exerts a pressure on actuator 730, causing it to deform into cavity 710 which, in turn, causes the non-compressible fluid within cavity 710 to exert a pressure on medical workpiece 10 thereby separating it from the delivery apparatus.

In each of the above examples of devices of this invention, the medical workpiece is shown attached directly to an adhesive layer or to a piezoelectric member. However, it is also possible, and is an aspect of this invention that a flexible connection designed to eliminate or alleviate uncontrolled movement of the delivery apparatus during placement and release of the medical workpiece may be incorporated into the device. For example, without limitation, such a device could be included within a delivery apparatus 50 or at point 13 in FIG. 5.

CONCLUSION

The medical workpiece detachment device and method herein have been described with reference to specific embodiments and aspects of the invention for the purpose of illustration and are not intended, nor are they to be construed, as limiting the scope of this invention in any manner whatsoever. Many alterations, modifications and variations on the embodiments described herein will become apparent to those skilled in the art based on the disclosures herein. All such alterations, modifications and variations are within the scope of this invention.

What is claimed:

1. A device for releasing a medical workpiece at a target site in a patient's body, comprising:
    an elongate member having a distal end;
    a piezoelectric member coupled to the elongate member at or near its distal end;
    a pair of electrical conducting members, each electrically coupled to the piezoelectric member; and
    a medical workpiece coupled to the distal end of the elongate member via a detachable joint, the detachable joint being incorporated into or otherwise operatively coupled with the piezoelectric member, such that vibration energy generated by passing an electrical current through the respective electrical conductors and piezoelectric member causes the workpiece to detach from the elongate member.

2. The device of claim 1, wherein the elongate member is a pusher wire.

3. The device of claim 1, wherein the elongate member is a microcatheter.

4. The device of claim 1, wherein the electrical conducting members comprise electrically conductive wires.

5. The device of claim 2, wherein the pusher wire comprises one of the electrical conducting members.

6. The device of claim 1, wherein the detachable joint comprises an adhesive layer disposed between the piezoelectric member and the workpiece, the adhesive layer comprising a proximal face that forms a first interfacial bond with a distal face of the piezoelectric member and a distal face that forms a second interfacial bond with a proximal face of the workpiece.

7. The device of claim 6, wherein the adhesive layer is susceptible to one or both of adhesive failure and cohesive failure.

8. The device of claim 7, wherein adhesive failure comprises failure of the interfacial bond between the piezoelectric member and the adhesive layer, failure of the interfacial bond between the adhesive layer and the workpiece, or both.

9. The device of claim 7, wherein cohesive failure comprises fracturing of the adhesive layer.

10. The device of claim 9, wherein the adhesive layer comprises one or more engineered structural flaws.

11. The device of claim 10, wherein the one or more engineered structural flaws comprise one or both of
    one or more discontinuities in one or both faces of the adhesive layer, and
    one or more internal discontinuities in the adhesive layer.

12. The device of claim 7, wherein the adhesive layer is selected from the group consisting of a glass, a ceramic, a metal and a polymer.

13. The device of claim 1, wherein the piezoelectric member comprises a fracturable piezoelectric substance.

14. The device of claim 13, wherein the fracturable piezoelectric substance comprises one or more engineered structural flaws.

15. The device of claim 14, wherein the one or more engineered structural flaw comprise one or both of
    one or more discontinuities in one or both faces of the piezoelectric substance, and
    one or more internal discontinuities in the structure of the piezoelectric member.

16. The device, of claim 13, wherein the fracturable piezoelectric substance is selected from the group consisting of a piezoelectric crystal, a piezoelectric ceramic, and a piezoelectric polymer.

17. The device of claim 1, wherein one of the piezoelectric member and the elongate member comprises a first coupling structure, and the medical workpiece comprises a second coupling structure that is at least partially complementary to the first coupling structure, such that, when the second coupling structure is in complementary alignment with the first coupling structure, the medical workpiece is releasably coupled to the delivery apparatus.

18. The device of claim 17, wherein one of the first and second coupling structures comprises a protrusion surface that has a selected shape and the other of the first and second coupling structures comprises a cavity surface that is at least partially complementary to the protrusion surface.

19. The device of claim 18, wherein the protrusion surface comprises a cylinder, cone, or truncated cone, and the cavity surface defines a corresponding cylindrical, conical, or truncated-conical void.

20. The device of claim 18, wherein the protrusion surface comprises a sphere having a diameter, and the cavity comprises at least one cross-sectional dimension which is complementary to the diameter of the sphere.

21. The device of claim 17, further comprising a lumen described by an inside surface of the piezoelectric member, the lumen having an axis aligned with an axis of the medical workpiece, and a plunger member slidably disposed within the lumen, wherein at least one cross-sectional dimension of the plunger is complementary to at least one cross-sectional dimension of the lumen, such that, when no electrical signal is being sent to the piezoelectric member, the plunger is releasably coupled to the piezoelectric member.

22. The device of claim 17, further comprising a cavity surface defining a cavity in a distal portion of the elongate member, and an actuator member that is either slidably disposed within the cavity or is coupled to the cavity surface, the actuator member directly or operatively coupled to the piezoelectric member, wherein at least a portion of the elongate member comprises the first coupling structure.

23. The device of claim 17, further comprising a cavity surface defining a cavity in a distal portion of the piezoelectric member, wherein at least a portion of a distal end of the piezoelectric member comprises the first coupling structure.

* * * * *